United States Patent [19]

Inagi et al.

[11] Patent Number: 4,474,798

[45] Date of Patent: Oct. 2, 1984

[54] PHARMACEUTICAL PREPARATION FOR ENDERMIC APPLICATION

[75] Inventors: Toshio Inagi, Tokorozawa; Masayuki Inoue, Higashi-Murayama; Toyojiro Muramatsu, Sayama, all of Japan

[73] Assignee: Kowa Co., Ltd., Nagoya, Japan

[21] Appl. No.: 488,587

[22] Filed: Apr. 25, 1983

[30] Foreign Application Priority Data

Apr. 30, 1982 [JP] Japan .................................. 57-72959

[51] Int. Cl.$^3$ ............................................ A61K 31/40
[52] U.S. Cl. .................................................. 424/274
[58] Field of Search ........................................ 424/274

[56] References Cited

PUBLICATIONS

Chem. Abst., 94-7725q (1981).
Chem. Abst., 95-86301d (1981).
Chem. Abst., 95-156602(v) (1981).
Remington's Pharmaceutical Sciences, 16th Ed. 1980, pp. 723-725, 1112.

Primary Examiner—Stanley J. Friedman
Attorney, Agent, or Firm—Oblon, Fisher, Spivak, McClelland & Maier

[57] ABSTRACT

A pharmaceutical preparation for endermic application is disclosed which comprises indomethacin and at least one solubilizer selected from the group consisting of a $C_{10}$ terpenoid and a $C_{10}$ phenol.

8 Claims, No Drawings

PHARMACEUTICAL PREPARATION FOR ENDERMIC APPLICATION

BACKGROUND OF THE INVENTION

1. Field of the Invention

This invention relates to a novel preparation of indomethacin for endermic application.

2. Description of the Prior Art

Indomethacin is an excellent non-steroidal, analgesic and antiphlogistic agent. It can however be hardly dissolved in water nor in various solvents which are generally usable as bases for endermic application. Indomethacin is slightly dissolvable in benzyl alcohol, tetrahydrofuran, dimethylsulfoxide, dimethylformamide and the like. The indomethacin solutions thus dissolved suffer some problems in the formation of a preparation suitable for endermic application, from both viewpoints of the concentration and potency of indomethacin. Therefore, indomethacin has been heretofore administered in the form of an oral preparation.

The present inventors have made many studies of preparations of indomethacin for endermic application and have already succeeded in obtaining an endermically-applicable preparation having excellent absorptivity through the skin by incorporating indomethacin in an alcohol-water system and then forming the resultant mixture into a gelated ointment, as disclosed in Japanese Patent Publication No. 10886/1981. Such gelated ointment has been recently marketed and has been found highly valuable in its clinical application.

The present inventors have conducted continuous research with a view toward developing new dosable forms of the endermically-applicable indomethacin preparation and bases therefor. As a result, it has been discovered that certain types of terpenoids and phenols can enhance the solubiliy and stability of indomethacin in bases and hence permit indomethacin to be incorporated in a variety of bases for endermic application. This discovery has led to the present invention.

SUMMARY OF THE INVENTION

This invention provides a pharmaceutical preparation for endermic application, which comprises indomethacin and one or more solubilizers selected from the group consisting of $C_{10}$ terpenoids and $C_{10}$ phenols.

DETAILED DESCRIPTION OF THE PREFERRED EMBODIMENTS

Eligible terpenoids having 10 carbon atoms and useful as solubilizers in the practice of the invention include hydrocarbonaceous terpenes such as limonene, pinene, camphene and cymene; alcoholic terpenes such as citronellol, geraniol, nellol, linalol, menthol, terpineol, rosinol, borneol and iso-borneol; and ketone-type terpenes such as menthone and camphor. On the other hand, eligible phenols having 10 carbon atoms include thymol, safrole, iso-safrole, eugenol, iso-eugenol and the like. These solubilizers may be used singly or in combination. The content of such solubilizers when used either alone or in combination may vary depending on the content of indomethacin and the type and amount of a solvent utilized. However, the solubilizers are capable of producing satisfactory results when incorporated in a total amount of 0.3-10% by weight.

Eligible solvents useful in dissolving indomethacin include alcohols such as ethanol and propanol; mixed alcohol-water systems; glycols such as butylene glycol and propylene glycol; vegetable oils such as olive oil and soybean oil; liquid higher fatty acids such as oleic acid, linoleic acid and linolenic acid; higher alcohols such as octyl alcohol and hexadecyl alcohol; hydrocarbons such as paraffin and squalane; esters of $C_4$–$C_{14}$ monocarboxylic acids and $C_1$–$C_5$ alcohols; and diesters of $C_4$–$C_{10}$ dicarboxylic acids and $C_1$–$C_3$ alcohols.

A pharmaceutical preparation for endermic application according to the invention may be produced by dissolving indomethacin together with at least one solubilizer in one or more of the above-described solvents, or by further incorporating the thus formed solution in another base for endermic application. Preferably, indomethacin is added in an amount of 0.1-5% by weight.

Eligible forms of the pharmaceutical preparation for endermic application which are obtainable in such manner include, for example, a liquid preparation, an ointment, a gelated ointment, cream, a plaster and the like.

Since the addition of one or more of these solubilizers in a small amount can significantly increase the solubility and stability of indomethacin in various solvents, the resultant indomethacin solutions may be incorporated in a wide variety of bases for endermic application, thus providing endermically-applicable preparations of various forms. Thus, the solubilizers contemplated by the invention are extremely effectively useful.

The invention will now be described in further detail with reference to certain specific experiment and preparation examples which are provided for illustration purposes only and are not construed to be limiting.

Experiment 1:

Solubility Test on Indomethacin

A large excess of indomethacin was added to each of a variety of solvents, followed by addition of one of the solubilizers given in Table 1. The resultant mixture was shaken for 24 hours at 25° C. and then subjected to centrifugal separation. The supernatant was collected. The content of indomethacin in the supernatant was determined by the UV method or the HPLC method and compared with that in a supernatant having no stabilizer added thereto. The results are shown in Tables 1 and 2.

TABLE 1

| Solvent | None (Weight dissolved) (mg/ml) | l-Menthol 3% | l-Menthol 5% | l-Menthol 10% |
|---|---|---|---|---|
| 100% Ethanol | 100 (17.4) | 130 | 140 | 150 |
| 80% Ethanol | 100 (8.0) | 140 | 200 | 270 |
| 60% Ethanol | 100 (2.4) | 160 | 350 | 440 |
| 50% Ethanol | 100 (0.75) | 350 | x | x |

TABLE 1-continued

| Solvent | Solubilizer | | | |
|---|---|---|---|---|
| | None (Weight dissolved) (mg/ml) | l-Menthol 3% | l-Menthol 5% | l-Menthol 10% |
| Isopropyl myristate | 100 (1.3) | 210 | x | x |
| Octylodecyl myristate | 100 (0.5) | 190 | x | x |
| Propanol | 100 (7.5) | 180 | x | x |

Note:
The figures are expressed in terms of percentage to the weight of indomethacin dissolved without any solubilizer added in their corresponding solvents.
The symbol x indicates that the solubilizer was not dissolved in the solvent.

TABLE 2

| Solubilizer | Solvent | | | |
|---|---|---|---|---|
| | 100% Ethanol | 80% Ethanol | 60% Ethanol | 50% Ethanol |
| None (weight dissolved) (mg/ml) | 100 (17.4) | 100 (8.0) | 100 (2.4) | 100 (0.75) |
| dl-Camphor 3% | 120 | 150 | 170 | 270 |
| dl-Camphor 5% | 160 | 190 | 230 | 400 |
| dl-Camphor 10% | 200 | 230 | 390 | x |
| Eugenol 3% | 140 | 160 | 170 | x |
| Eugenol 5% | 400 | 190 | 250 | x |
| D-limonene 3% | 140 | 170 | x | x |
| D-limonene 5% | 250 | 200 | x | x |

Note:
The figures and the symbol x have the same significance as given in Table 1.

Preparation Example 1: (Ointment)

| Indomethacin | 0.5 (wt. %) |
|---|---|
| Geraniol | 5.0 |
| Eugenol | 5.0 |
| Vaseline | 80.5 |
| Solid paraffin | 5.0 |
| Cetanol | 2.0 |
| Isopropyl myristate | 2.0 |

Preparation Example 2: (Gelated Preparation)

| Indomethacin | 1.0 (wt. %) |
|---|---|
| l-Menthol | 3.0 |
| Propylene glycol | 12.0 |
| Carboxyvinyl polymer (CARBOPOLE 934) | 1.0 |
| Diisopropanol amine | 1.0 |
| Ethanol | 40.0 |
| Purified water | Balance to 100.0 |

Preparation Example 3: (Liquid Preparation)

| Indomethacin | 2.0 (wt. %) |
|---|---|
| l-Menthol | 10.0 |
| Ethanol | 45.0 |
| Aqueous ammonia (10%) | 0.2 |
| Purified water | Balance to 100.0 |

Preparation Example 4: (O/W Cream)

| Indomethacin | 0.8 (wt. %) |
|---|---|
| Camphor | 2.0 |
| Diisopropyl adipate | 20.0 |
| Chrotamiton | 2.0 |
| Glyceryl monostearate | 10.0 |
| Polyoxyethylene cetyl ether | 3.0 |
| Methylparaben | 0.1 |
| Propylparaben | 0.1 |

| -continued | |
|---|---|
| Purified water | Balance to 100.0 |

Preparation Example 5: (Plaster)

| Indomethacin | 1.0 (wt. %) |
|---|---|
| Methyl salicylate | 2.0 |
| l-Menthol | 3.0 |
| Diethyl sebacate | 5.0 |
| Raw rubber | 40.0 |
| Zinc flower | 20.0 |
| Rosin | 29.0 |

This invention now being fully described, it should be noted that various changes and modifications may be made thereto without departing from the spirit or scope of the invention as set forth herein.

What is claimed is:

1. A pharmaceutical preparation for endermic application, comprising
   (a) a pharamaceutically effective amount of indomethacin and
   (b) an indomethacin-solubilizing amount of at least one solubilizer selected from the group consisting of limonene, pinene, camphene, cymene, citronellol, geraniol, nellol, linalol, menthol, terpineol, rosinol, borneol, iso-borneol, menthone, camphor, thymol, safrole, iso-safrole, eugenol, and iso-eugenol.

2. The pharmaceutical preparation according to claim 1, wherein said indomethacin is present in an amount of 0.1–5% by weight of the preparation.

3. The pharmaceutical preparation according to claim 1, wherein said solubilizer is present in a total amount of 0.3–10% by weight of the preparation.

4. The pharmaceutical preparation according to claim 1 or 3, wherein said solubilizer is selected from the group consisting of limonene, pinene, camphene, cymene, citronellol, geraniol, nellol, linalol, menthol, terpineol, rosinol, borneol, iso-borneol, menthone and camphor.

5. The pharmaceutical preparation according to claim 1 or 3, wherein said solubilizer is selected from the group consisting of thymol, safrole, iso-safrole, eugenol and iso-eugenol, 6. The pharmaceutical preparation of claim 1, further comprising
(c) a solvent selected from alcohol, an alcoholwater mixture, glycols, vegetable oils, liquid higher fatty acids, higher alcohols, paraffin, squalane, esters of $C_4$–$C_{14}$ monocarboxylic acids and $C_1$–$C_5$ alcohols, diesters of $C_4$–$C_{10}$ dicarboxylic acids and $C_1$–$C_3$ alcohols and mixtures thereof, in an amount effective to dissolve (a) and (b).

7. The pharmaceutical preparation of claim 6, wherein the alcohol is ethanol or propanol; the glycol is butylene glycol; the vegetable oil is olive oil or soybean oil; the liquid higher fatty acids are oleic acid, linoleic acid or linolenic acid; the higher alcohols are octyl alcohol or hexadecyl alcohol, and the hydrocarbons are paraffin or squalene.

8. The pharmaceutical preparation of claim 1 in the form of a liquid preparation, an ointment, a gelated ointment, a cream or a plaster.

* * * * *